(12) United States Patent
Murata et al.

(10) Patent No.: US 9,733,567 B2
(45) Date of Patent: Aug. 15, 2017

(54) RETICLE TRANSMITTANCE MEASUREMENT METHOD, AND PROJECTION EXPOSURE METHOD USING THE SAME

(71) Applicant: SEIKO INSTRUMENTS INC., Chiba-shi, Chiba (JP)

(72) Inventors: Michihiro Murata, Chiba (JP); Yutaka Gomi, Chiba (JP)

(73) Assignee: SII Semiconductor Corporation (JP)

( * ) Notice: Subject to any disclaimer, the term of this patent is extended or adjusted under 35 U.S.C. 154(b) by 0 days.

(21) Appl. No.: 14/859,781

(22) Filed: Sep. 21, 2015

(65) Prior Publication Data

US 2016/0091391 A1   Mar. 31, 2016

(30) Foreign Application Priority Data

Sep. 30, 2014   (JP) ................................ 2014-202016
Mar. 17, 2015   (JP) ................................ 2015-053800

(51) Int. Cl.
| | | |
|---|---|---|
| *G01N 21/00* | (2006.01) | |
| *G03F 7/20* | (2006.01) | |
| *G01N 21/956* | (2006.01) | |
| *G01M 11/02* | (2006.01) | |
| *G01N 21/59* | (2006.01) | |

(52) U.S. Cl.
CPC ........... *G03F 7/20* (2013.01); *G01M 11/0285* (2013.01); *G01N 21/956* (2013.01); *G03F 7/70666* (2013.01); *G03F 7/70941* (2013.01); *G01N 2021/5919* (2013.01); *G01N 2021/95676* (2013.01)

(58) Field of Classification Search
CPC ............. G03F 7/70341; G03F 7/70358; G03F 7/70591; G03F 7/7055; G03F 7/70483; G01N 2021/95676; G01N 21/956; G03B 27/72
USPC .......... 356/432–440, 399–401, 237.1–237.5, 356/121–123; 355/53, 55, 67; 430/5, 22, 430/30, 312
See application file for complete search history.

(56) References Cited

U.S. PATENT DOCUMENTS

| | | | | |
|---|---|---|---|---|
| 5,864,433 A | * | 1/1999 | Takahashi ........... | G02B 27/0025 250/548 |
| 2002/0080338 A1 | * | 6/2002 | Taniguchi ........... | G03F 7/70058 355/67 |
| 2005/0041226 A1 | * | 2/2005 | Tanaka ................ | G03F 7/70241 355/53 |

(Continued)

OTHER PUBLICATIONS

Abstract, Publication No. 06-236838, Publication Date Aug. 23, 1994.

(Continued)

*Primary Examiner* — Hoa Pham
(74) *Attorney, Agent, or Firm* — Adams & Wilks

(57) ABSTRACT

When a reticle is first used, the reticle is loaded in a projection exposure device and measured by either oblique measurement and random measurement, thereby avoiding the fear of uneven sampling and determining the reticle transmittance of the entire reticle as the parent population, without increasing the sampling count. The same effect can be obtained by making the measurement spot size, which is fixed in general, variable and by changing the angle of incidence in relation to the measurement spot size.

3 Claims, 6 Drawing Sheets

Present: Diagonal

(56) References Cited

U.S. PATENT DOCUMENTS

2007/0218673 A1\* 9/2007 Nakamura ................ G03F 1/36
　　　　　　　　　　　　　　　　　　　　　　　438/597
2012/0120379 A1\* 5/2012 Phillips .................... F28F 3/12
　　　　　　　　　　　　　　　　　　　　　　　355/52

OTHER PUBLICATIONS

Abstract, Publication No. 2001-297961, Publication Date Oct. 26, 2001.

\* cited by examiner

Conventional: Equal interval along X and Y

Present: Diagonal

Conventional: Equal interval along X and Y

Present: Random

RETICLE TRANSMITTANCE MEASUREMENT METHOD, AND PROJECTION EXPOSURE METHOD USING THE SAME

BACKGROUND OF THE INVENTION

1. Field of the Invention

The present invention relates to a method of measuring a transmittance of a reticle that is used in manufacture of a semiconductor device, and a projection exposure device (projection aligner) and a projection exposure method that are used in the measurement.

2. Description of the Related Art

In a projection exposure device, for example, a stepper, when a reticle is first used, the reticle is actually loaded in the device to be exposed to light from a mercury lamp serving as a light source, and (transmitted energy/incident energy) is calculated as a reticle transmittance. Sampling is carried out through the exposure at an equal interval over the entire reticle patterns. Then estimation on characteristics is required over the entire reticle viewed as a parent population. However the sampling tends to be uneven since it is difficult in practice to recognize what pattern is there on the reticle. For example, in the case of a pattern that is repeated at the same pitch as that of the sampling, the result calculated as the reticle transmittance is far from the real value. A correction function is activated in projection exposure devices when the amount of transmitting light increases, in order to cancel out the effect of lens expansion from heat that is generated by the increased exposure load. However, incorrect feedback leads to a focus shift, causing an increase in line width fluctuation and a failure in maintaining the rectangular resist profile, which deteriorates formation of a desired pattern. Shorts and opens consequently develop in the wiring pattern, thereby impairing quality.

Increasing the sampling count has therefore been tried in an attempt to capture the entire picture of the reticle as the parent population. However, the fear of uneven sampling remains in the case of equal interval measurement and, even if accurate measurement is somehow managed, the vast amount of time required in this approach impairs the productivity of the projection exposure device.

As described in the description of the related art, the problem of a mismatch between the result acquired as the reticle transmittance and the real value may occur when a pattern repeated at the same pitch as that of the sampling is included. In the case where a reticle transmittance that takes into account the characteristics of patterns is determined, for example, one method of determining the reticle transmittance, when a different shot has a different area as in Japanese Published Patent Application No. 2001-297961, involves conducting total light amount measurement on the entire reticle surface, storing data about a projected image, and calculating an actually exposed portion of the reticle from the stored data and from the opening/closing of a masking blade. A prerequisite for the calculation of an actually exposed portion of the reticle is that accurate total light amount measurement on the entire reticle surface can be conducted first. When a pattern repeated at the same pitch as that of the sampling is included, a result calculated as the reticle transmittance does not match reality, which makes it difficult to calculate an actually exposed portion of the reticle from the opening/closing of the masking blade.

Increasing the sampling count in an attempt to capture the entire picture of the reticle as the parent population is a way to measure the reticle transmittance accurately. Another method of determining the reticle transmittance is described in Japanese Published Patent Application No. H06-236838, in which a reticle is actually loaded in a projection exposure device to be exposed to light from a mercury lamp serving as a light source, and image data of a transfer image of a reticle pattern formed by the exposure is input to be used in the calculation of the reticle transmittance. However, both methods have a problem in that the huge sampling count requires a vast amount of time for measurement and accordingly impairs the productivity of the projection exposure device.

SUMMARY OF THE INVENTION

The present invention has been made in view of those problems, and it is an object of the present invention to provide, as a countermeasure for a focus shift that is caused by lens expansion due to increased exposure load in a projection exposure device, a novel measurement method and a novel projection exposure device that are applicable to reticle transmittance measurement for the calculation of a load used in the correction of exposure load.

In order to attain this object, a semiconductor device exposure method according to one embodiment of the present invention uses the following measures.

When a reticle is used first, the reticle is actually loaded in a projection exposure device and measured by one of oblique measurement and random measurement, thereby avoiding the fear of uneven sampling and capturing the entire picture of the reticle as the parent population, without increasing the sampling count. Results acquired as the reticle transmittance in this manner closely matches reality. In addition, the measurement spot size, which is fixed in the related art, may be made variable in the one embodiment of the present invention so that the same effect can be obtained by changing the angle of incidence in relation to the measurement spot size.

The reticle transmittance of the entire reticle is determined by measuring, in sampling, the transmittance of at least one chip area in a multi-patterned reticle that has a plurality of identical chips.

In order to determine the reticle transmittance in a short time without actually measuring the reticle transmittance, by making a different use of design data of a reticle pattern, there is employed an exposure method including: creating design data of a reticle pattern with the use of a standard CAD tool; executing data conversion in which the design data is converted into a standard file format such as the GDS II stream format or the CIF format, in a manner written by mask CAD; determining the reticle transmittance from the converted design data; and saving the determined reticle transmittance. Further, there are employed a semiconductor exposure device and exposure method for determining the reticle transmittance directly from data, without measuring the reticle transmittance of an actual reticle.

According to the one embodiment of the present invention, there may be provided, as a countermeasure for the focus shift that is caused by lens expansion due to increased exposure load in the projection exposure device, a method of determining the reticle transmittance with high precision in a short time no matter what characteristics a pattern has, that is, a method of determining an accurate reticle transmittance without impairing productivity.

DETAILED DESCRIPTION OF THE EMBODIMENTS

Figure 1:
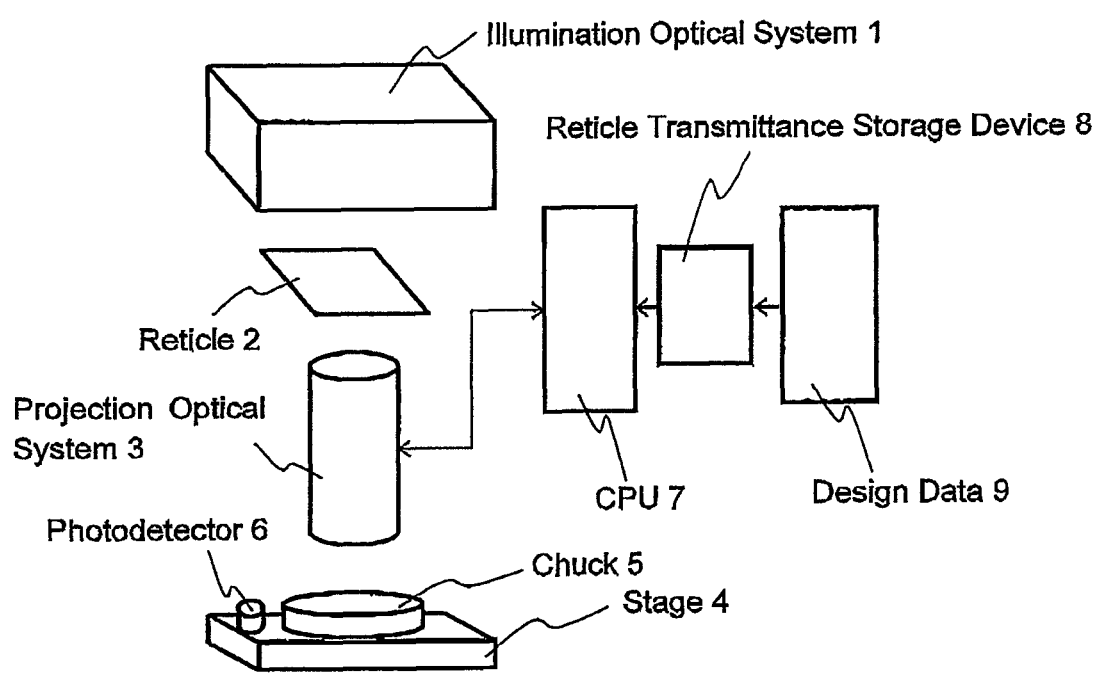
FIG. 1 is a block diagram of a stepper according to an embodiment of the present invention.

FIG. 1 is a block diagram of a stepper, which is one of projection exposure devices, according to an embodiment of the present invention. The stepper has a function of correcting exposure load based on design data. The stepper includes an illumination optical system 1 a reticle 2, which is an original plate for actually measuring the reticle transmittance, a projection optical system 3 for transferring by exposure a desired reticle pattern that is reduced in size to, for example, ⅕ onto a wafer, a stage 4 for moving the wafer to a given measurement spot where the reticle transmittance is measured, a chuck 5, which supports the wafer, a photodetector 6, which measures the amount of light passed through the projection optical system, and a CPU 7, which corrects exposure load based on a measured reticle transmittance, which calculates the reticle transmittance from design data to correct exposure load, and which controls the driving of the illumination optical system 1 and of the stage 4.

A reticle transmittance storage device 8 is a storage device for saving data of an actually measured reticle transmittance and data of a reticle transmittance that is calculated from design data 9. The method that uses the design data 9 is described later.

Figure 2:
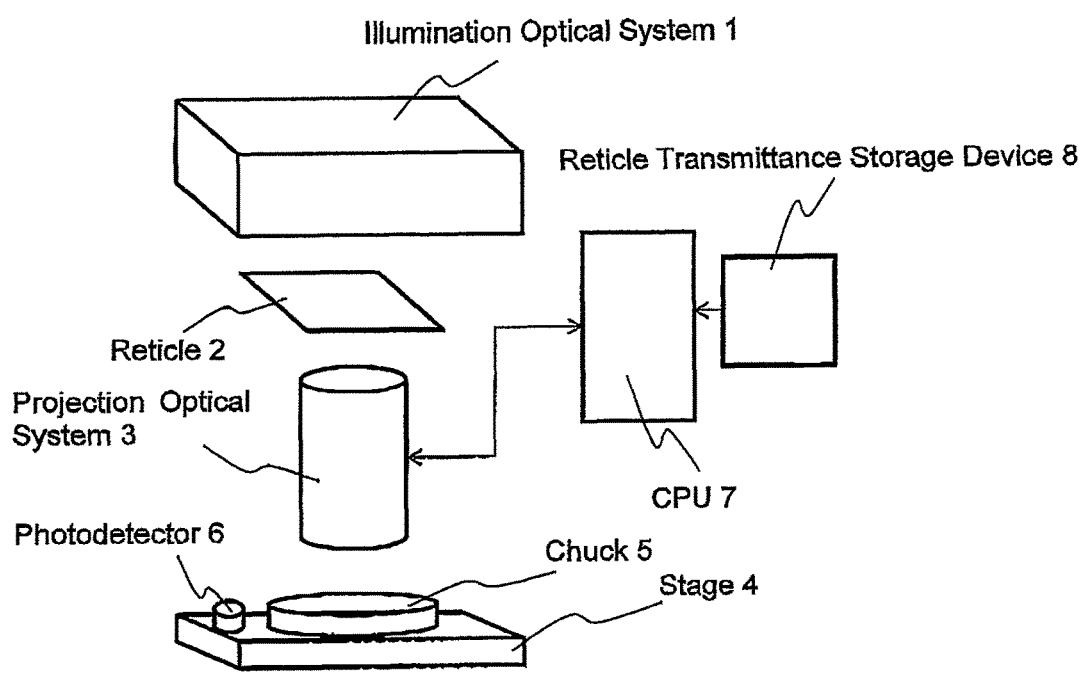
FIG. 2 is a block diagram of a stepper of the related art.

For reference, a block diagram of a stepper of the related art is illustrated in FIG. 2. An apparent difference is that the stepper of the related art does not involve associating the reticle transmittance with design data, and a reticle transmittance storage device 8 of the related art does not make use of data of a reticle transmittance that is calculated from design data.

With use of the above-mentioned structure, when a pattern repeated at the same pitch as that of the sampling, the problem of the related art, in which a result calculated as the reticle transmittance does not match reality, may be solved. A specific description is given below on methods of measuring the reticle transmittance.

Figure 3A:
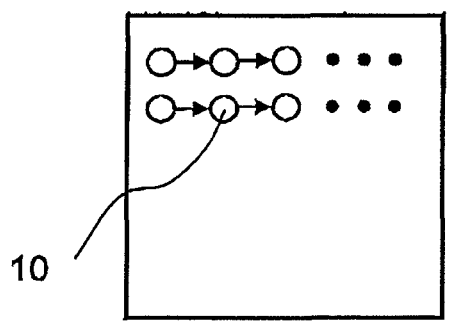
FIG. 3 is an explanatory diagram for illustrating a method of measuring the reticle transmittance by oblique measurement.
Figure 3B:
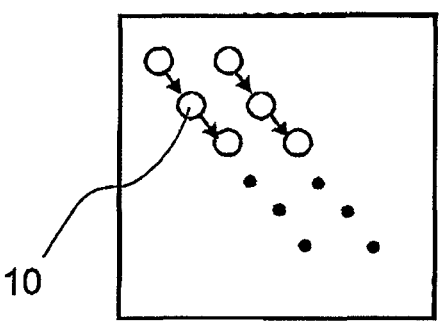

A first method involves, as illustrated in FIG. 3, putting a light amount measurement spot 10 on an oblique route that runs diagonally relative to the reticle, for example, and measuring at a 0.2-mm pitch, as opposed to the related art where measurement is made at a 0.2-mm pitch in an X-direction and a Y-direction, for example. The meaning of an oblique route running diagonally relative to the reticle is a route running along a straight line that is slanted relative to the four sides of the reticle and that does not usually match any diagonal line of the reticle. The measurement spot in this case is set so that the sampling in the X-direction and the Y-direction is conducted at a pitch different from the repetition pitch of a reticle pattern. The transmittance may also be measured by putting the measurement spot 10 on an oblique route that runs diagonally relative to the reticle and switching the pitch, for example, from 0.2 mm to 0.3 mm, back to 0.2 mm, and then to 0.3 mm. In this case too, the measurement spot is set so that the sampling in the X-direction and the Y-direction does not match with a reticle pattern having the same repetition pitch as the sampling pitch and matches with a reticle pattern having a different pitch.

A reticle transmittance that represents the overall characteristics of the reticle is determined from the sampling described above, and is saved in the reticle transmittance storage device 8. Based on the determined reticle transmittance, the CPU (exposure load correcting device) 7 of FIG. 1 corrects exposure load by correcting focus, lens distortion, and magnification in combination as needed, and sends feedback to the projection optical system 3 of FIG. 1 to perform projection exposure.

Figure 4A:
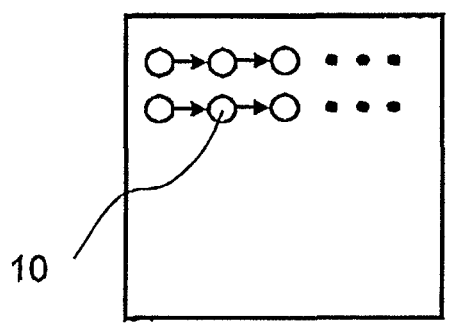
FIG. 4 is an explanatory diagram for illustrating a method of measuring the reticle transmittance by random measurement.
Figure 4B:
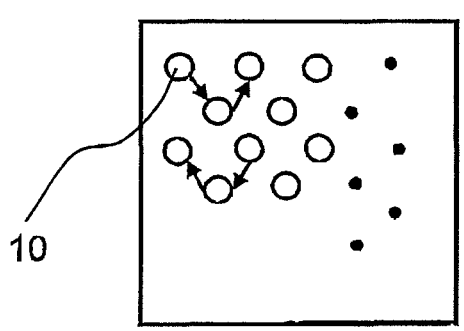

A second method involves, as illustrated in FIG. 4, giving the pitch of the measuring spot 10 a range of 0.2 mm to 1.0 mm, for example, as opposed to the related art where measurement is made at a 0.2-mm pitch by moving measurement spots in order in the X-direction and the Y-direction, for example. In the second method, the measurement spots, which are moved individually in the X-direction and the Y-direction in the related art, are combined and moved randomly in order to perform measurement with no regularity, and the sampling operation is set so as to match not with a reticle pattern that has the same repetition pitch as the sampling pitch but with a reticle pattern that has a different pitch.

Figure 5:
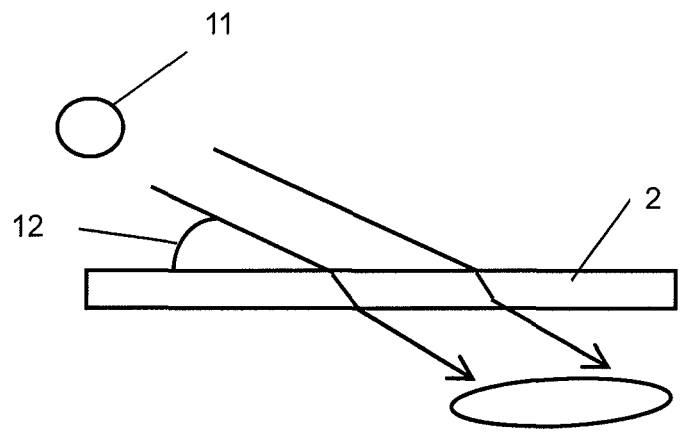
FIG. 5 is an explanatory diagram for illustrating a method of angled measurement that is suited to a small measurement spot size.
Figure 6:
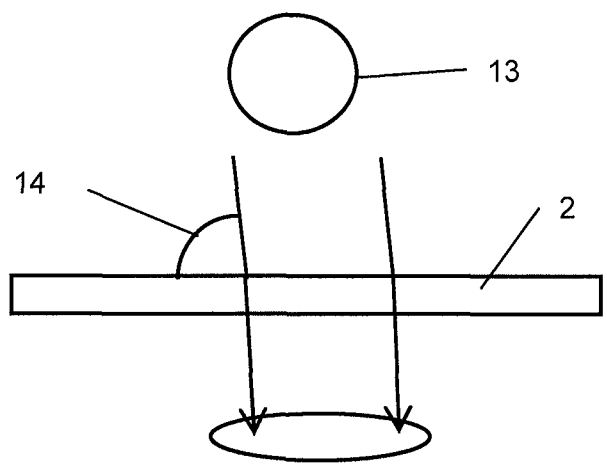
FIG. 6 is an explanatory diagram for illustrating a method of angled measurement that is suited to a large measurement spot size.

A third method involves, as illustrated in FIG. 5, making the diameter (Φ) of the measurement spot variable between 0.3 mm and 1.0 mm and changing the angle of inclination to suit the measurement spot size, as opposed to the related art where the diameter (Φ) of the measurement spot is fixed at 0.3 mm, for example. When the size of a measurement spot 11 viewed from the front is small, for example, when the measurement spot 11 is 0.3 mm in diameter (Φ), the reticle transmittance is measured by setting a small angle between 10 degrees and 30 degrees to an inclination angle θ1 (12) with respect to a surface of the reticle 2 viewed edge-on. This secures a large effective measurement area despite the small size of the measurement spot. When the size of a measurement spot 13 viewed from the front is large, for example, when the measurement spot 13 is 1.0 mm in diameter (Φ) as illustrated in FIG. 6, on the other hand, the reticle transmittance can be measured by setting a large angle between 70 degrees and 90 degrees to an inclination angle θ2 (14) with respect to the surface of the reticle 2 viewed edge-on. This is because a large measurement area can be secured when the measurement spot size is large. Varying the measurement spot size in this manner prevents sampling that is conducted at the same pitch as the repetition pitch of a reticle pattern.

Figure 7:
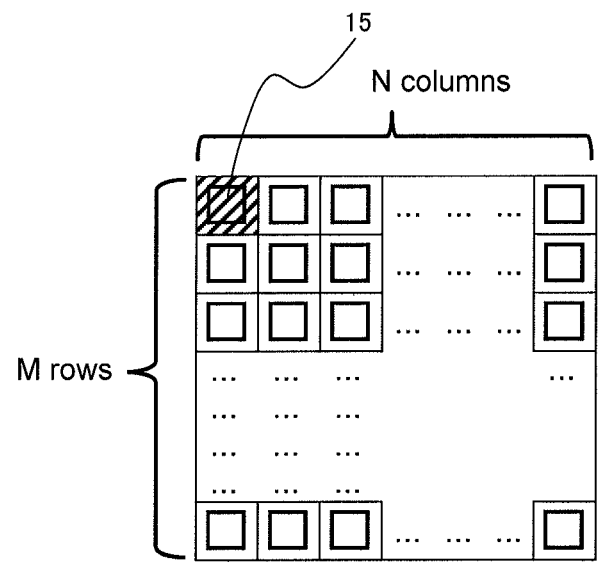
FIG. 7 is an explanatory diagram for illustrating a method of measuring the transmittance of one chip area.

A fourth method involves, as illustrated in FIG. 7, measuring the transmittance by sampling only one chip area in a multi-patterned reticle that includes a plurality of identical chips, and calculating the reticle transmittance from the result of the measurement. The one chip area, which is denoted by 15, is, for example, a unit area surrounded by an area that reaches the center (midpoint) of scribe lines along which the wafer is cut in dicing, inside and outside the operating area of a semiconductor device. The entire multi-patterned area is the entire reticle surface, which includes all these unit areas. Parameters for these are input to the projection exposure device in advance as a sampling area and the entire multi-patterned area. The reticle transmittance for the entire reticle is determined by calculating an area dimension ratio of the one chip area 15 and the entire multi-patterned area, and is saved in the reticle transmittance storage device 8. Based on the determined reticle transmittance, the CPU (exposure load correcting device) 7 of FIG. 1 corrects exposure load by correcting focus, lens distortion, and magnification in combination as needed, and sends feedback to the projection optical system 3 of FIG. 1 to perform projection exposure.

Figure 8:
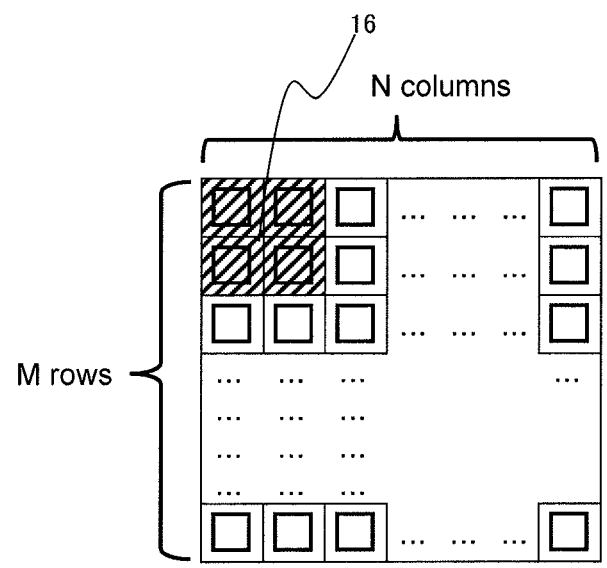
FIG. 8 is an explanatory diagram for illustrating a method of measuring the transmittance of four chip areas.

A fifth method involves, as illustrated in FIG. 8, measuring the transmittance by sampling only four chip areas 16 in a multi-patterned reticle that includes a plurality of identical chips, and calculating the reticle transmittance from the result of the measurement. The reticle transmittance of the entire reticle surface is determined by calculating an areal dimension ratio of the four chip areas 16 and the entire multi-patterned area, and the same exposure load correction as in the fourth method is thus accomplished.

Figure 9:
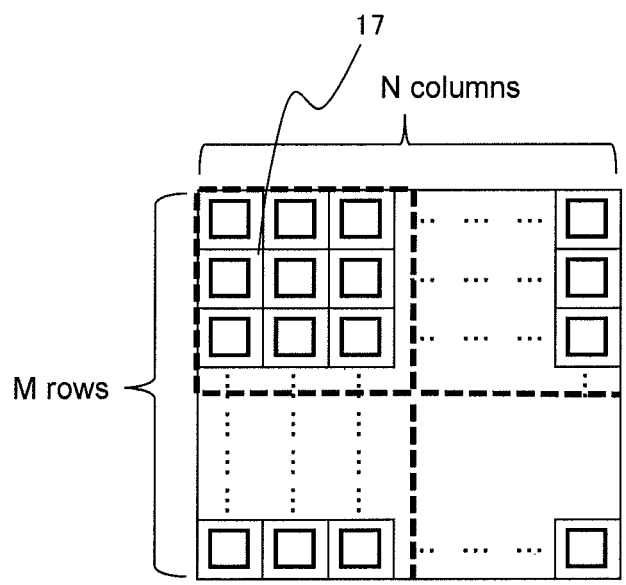
FIG. 9 is an explanatory diagram for illustrating a method of measuring only the transmittance of arbitrarily selected areas.

A sixth method involves, as illustrated in FIG. 9, measuring the transmittance by sampling only a selected area 17, which is ¼ of the entire reticle in a multi-patterned reticle that includes a plurality of identical chips, and calculating the reticle transmittance from the result of the measurement. The reticle transmittance of the entire reticle surface is determined by calculating an areal dimension ratio of the selected area 17, which is ¼ of the entire reticle, and the entire multi-patterned area, and the same exposure load correction as in the fourth and fifth methods is thus accomplished while reducing a measurement time to ¼ of a normal measurement time.

A seventh method differs from the methods described above, and determines the reticle transmittance without actually measuring the transmittance. In order to obtain the design data 9 of FIG. 1, design data of a reticle is created first for all layers by CAD. Data conversion is executed next to convert the design data into a standard file format such as the GDS II stream format or the CIF format. The converted data and the areal dimensions that a light shielding film takes up on the reticle are used to determine the reticle transmittance. The determined reticle transmittance is saved as data in the reticle transmittance storage device 8 of FIG. 1 via a local area network (LAN). Based on the reticle transmittance saved as data, the CPU (exposure load correcting device) 7 of FIG. 1 corrects exposure load by correcting focus, lens distortion, and magnification in combination as needed, and sends feedback to the projection optical system 3 of FIG. 1. The reticle transmittance can be determined in a short time without measuring the transmittance of an actual reticle in this manner. A comparison of the reticle transmittance thus determined without measuring with the reticle transmittance that is determined through measuring by one of the first to sixth methods is useful in improving the precision of determining the reticle transmittance from CAD data or in accomplishing appropriate sampling in measurement, which further improves precision.

The present invention is applicable to the manufacture of a device that requires micro-fabrication in which a projection exposure device uses a reticle and photolithography technology in one of processes, such as a semiconductor substrate or a MEMS.

What is claimed is:

1. A reticle transmittance measurement method for a projection exposure device configured to project a pattern of a reticle onto a wafer to obtain a given pattern on the wafer, the reticle transmittance measurement method comprising:

sampling a transmittance of the reticle by measuring the transmittance of the reticle along an oblique route that runs diagonally relative to the reticle, with a sampling pitch being set so as to match with a different pattern of a reticle pattern that has a same repetition pitch, and not to match with a same pattern of the reticle pattern that has the same repetition pitch.

2. A projection exposure method, comprising performing exposure load correction based on a reticle transmittance that is determined by the reticle transmittance measurement method of claim 1.

3. A projection exposure method according to claim 2, wherein the exposure load correction comprises at least one of focus correction, lens distortion correction, or magnification correction.

* * * * *